United States Patent
Choi et al.

[11] Patent Number: 5,771,705
[45] Date of Patent: Jun. 30, 1998

[54] OPERATING METHOD FOR AIR CONDITIONER

[75] Inventors: Ho Seon Choi, Seoul; Dae-Keun Lee, Kyungki-Do; See-Poong Seong; Deok Huh, both of Seoul, all of Rep. of Korea

[73] Assignee: LG Electronics, Rep. of Korea

[21] Appl. No.: 712,142

[22] Filed: Sep. 11, 1996

[30] Foreign Application Priority Data

Sep. 22, 1995 [KR] Rep. of Korea ............... 1995-31440

[51] Int. Cl.[6] .............................. A61B 5/04; G05D 23/00
[52] U.S. Cl. ................................ 62/229; 236/51; 600/544
[58] Field of Search ........................... 62/229; 236/51, 236/47, 78 D; 600/544

[56] References Cited

U.S. PATENT DOCUMENTS

| | | | |
|---|---|---|---|
| 4,934,593 | 6/1990 | Meyer | 236/78 D |
| 5,626,145 | 5/1997 | Clapp et al. | 600/544 |

FOREIGN PATENT DOCUMENTS

| | | | |
|---|---|---|---|
| 0025015 | 3/1981 | Japan | 236/78 D |
| 403156240 | 7/1991 | Japan | 236/51 |

*Primary Examiner*—William E. Wayner
*Attorney, Agent, or Firm*—Ostrolenk, Faber, Gerb & Soffen, LLP

[57] ABSTRACT

An operating method for a room air conditioner(RAC) which is capable of enhancing an alertness level of a user based upon a human electroencephalogram(EEG), includes inputting an alertness operation mode key when the user desires to heighten an alertness degree of the user, performing an air conditioning operation to maintain a first standard temperature and a range of a temperature variation corresponding thereto to enhance the user's alertness degree, performing an air conditioning operation to maintain a second standard temperature and the range of the temperature variation corresponding thereto when the user feels cold at the first standard temperature, and to maintain a third standard temperature and the range of the temperature variation corresponding thereto when the user feels hot at the first standard temperature, repeating the second step when the user feels cold at the third standard temperature, and when the user feels hot at the second standard temperature, and performing an air conditioning operation according to a general mode when the user feels hot at the third standard temperature, and when the user feels cold at the second standard temperature.

11 Claims, 4 Drawing Sheets

| STANDARD TEMPERATURE(°C) | RANGE OF TEMPERATURE VARIATION(°C) |
|---|---|
| T1 | t1, t2, t3 |
| T2 | t1, t2, t3 |
| T3 | t1, t2, t3 |

OPERATING METHOD FOR AIR CONDITIONER

BACKGROUND OF THE INVENTION

1. Field of the Invention

The present invention relates to an operating method for an air conditioner, and in particular, to an improved operating method for an air conditioner which is capable of enhancing a degree of human alertness.

2. Description of the Prior Art

Generally, air conditioning means keeping an agreeable indoor atmosphere for the purpose of improving health or productivity by conditioning indoor air or air in a building with an air conditioner. In particular, for people, comfortable air conditioning can help to alleviate fatigue and to enhance productivity. Therefore, efforts have been made for creating an optimum working environment.

An air conditioner is an apparatus which takes in air, conditions it and then supplies it indoors, and available air conditioner types include a separate type air conditioner and a window type air conditioner. The separate type air conditioners may be classified into a room air conditioner (hereinafter, called RAC) and a package air conditioner.

FIG. 1 is a schematic block diagram of a RAC according to the conventional art. The RAC includes an indoor unit 10 and an outdoor unit 20. Here, the indoor unit 10 has an evaporator 11 which discharges cold air by causing air to flow around piping 30 carrying a low temperature liquid for heat exchange, and the outdoor unit 20 includes a compressor 21 for compressing a refrigerant gas at a low pressure to a high pressure gas, a condenser 22 for condensing the high temperature/high pressure gas into a high temperature and high pressure liquid by heat exchange to the outdoors, and an expansion valve 23 for converting the high temperature and high pressure liquid into a low temperature and low pressure liquid for heat exchange to the indoors.

The above-described conventional RAC is controlled by an operation program in a microcomputer 12 in the indoor unit 10.

First, a thermocouple(not illustrated) in the indoor unit 10 measures the indoor temperature and informs the microcomputer 12 of the measured temperature. Then, the microcomputer 12 turns on or off the compressor 21 in the outdoor unit 20 depending on the temperature measured by the thermocouple to operate the conventional RAC.

Referring to FIG. 2, the operation control of the conventional RAC will now be described in detail.

First, when a user sets a temperature of the RAC as 26° C. by remote control, an on/off temperature of the compressor 21 inputted in the microcomputer 12 becomes 26° C.±0.5° C. Accordingly, if the indoor temperature measured by the thermocouple gradually drops to 25.5° C., since the compressor 21 is turned off and is no longer being operable, the RAC is not operated. Then, when the indoor temperature rises to 26.5° C., since the indoor temperature is higher than the temperature set by the user(26.5° C.), the compressor 21 is operated again and then the RAC starts to operate.

That is, whatever temperature the user may set, the compressor 21 repeats the on/off operation to keep the indoor temperature constant.

However, according to the above-described operation method of the conventional RAC, by repeating the uniform on/off operation of the compressor, the operation is so standardized irrespective of an individual preference that it cannot satisfy individual demands.

Importantly, the user's alertness based on a working degree or a user's purpose has not been considered at all.

SUMMARY OF THE INVENTION

Accordingly, it is an object of the present invention to provide an improved operating method for a RAC which is capable of producing a maximum alertness to the user, pertaining to human electroencephalogram(hereinafter, called EEG).

To achieve the above object, there is provided a novel and useful operating method for a RAC according to the present invention which includes performing an air conditioning operation at a standard room temperature and a range of temperature variation above and below the standard room temperature set for enhancing an alertness level of a user and determined based upon alertness levels measured in a human electroencephalogram(EEG).

To achieve the above object, there is provided a novel and useful operating method for a RAC according to the present invention which includes inputting an alertness-enhancing operational mode key command when it is desired by a user to heighten an alertness degree of the user, performing an air conditioning operation for maintaining a first standard temperature and a range of temperature variation corresponding thereto to provide an optimum alertness degree in accordance with an alertness-enhancing operational mode, performing an air conditioning operation to maintain a second standard temperature and the range of temperature variation corresponding thereto when the user feels cold at the first standard temperature, and to maintain a third standard temperature and the range of temperature variation corresponding thereto when the user feels hot at the first standard temperature, repeating the second step when the user feels cold at the third standard temperature, and when the user feels hot at the second standard temperature, and performing an air conditioning operation in accordance with a general operational mode when the user feels hot at the third standard temperature, and when the user feels cold at the second standard temperature.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENTS

Figure 1:
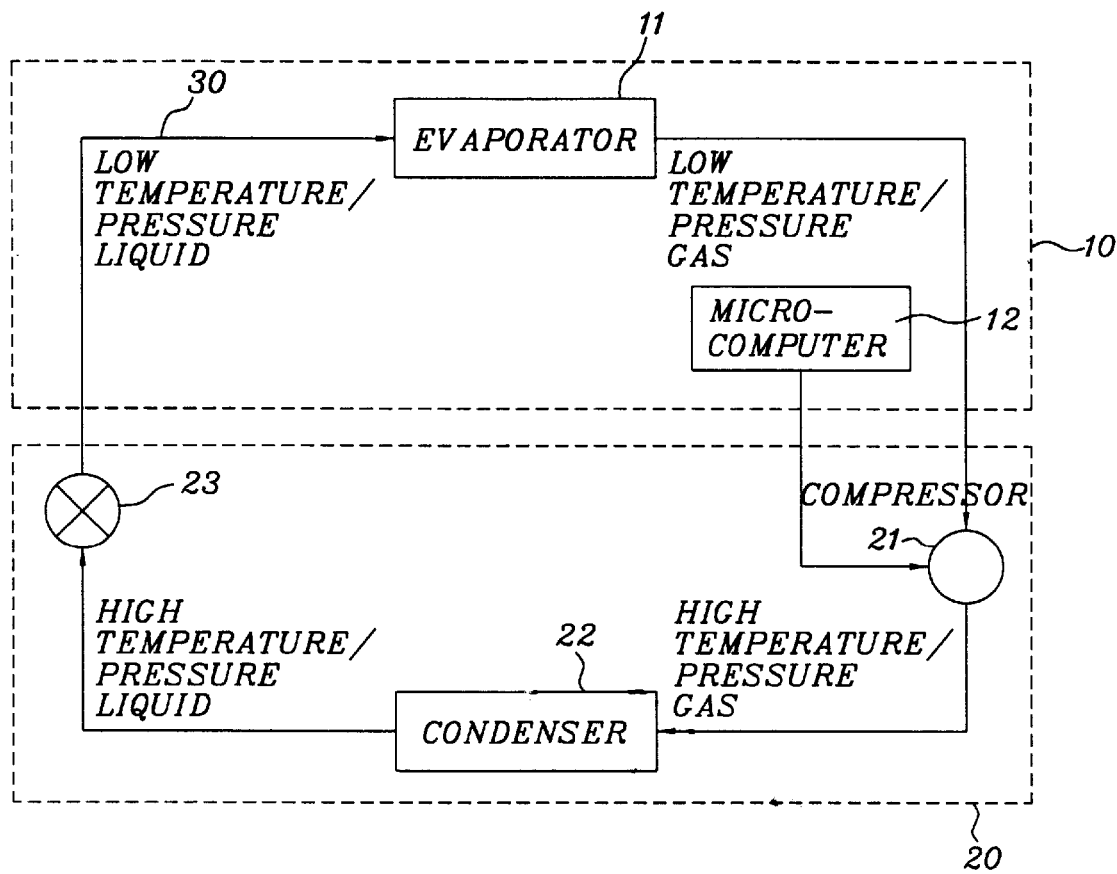
FIG. 1 is a schematic block diagram showing a conventional RAC.
Figure 2:
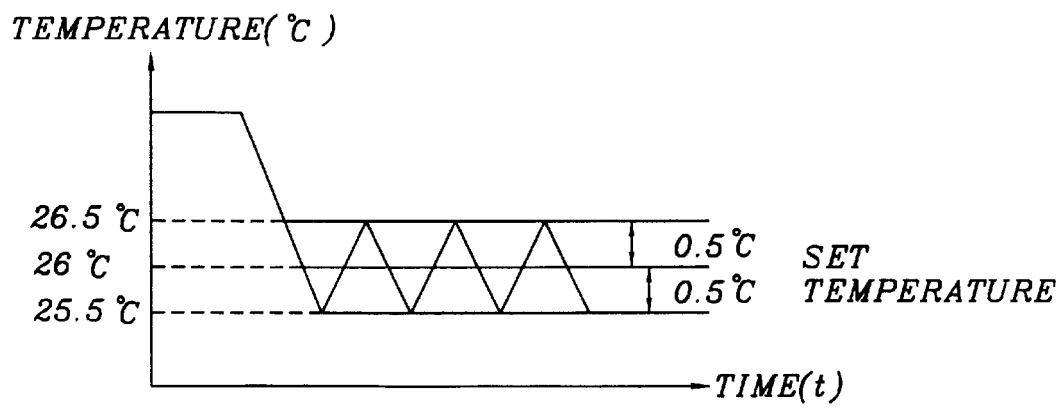
FIG. 2 is a graph showing a temperature characteristic of a thermocouple in the on/off operation of a compressor in the conventional RAC.
Figure 3:
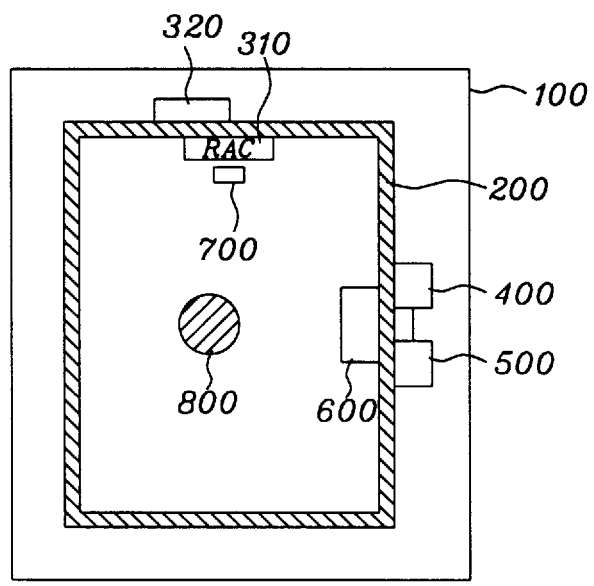
FIG. 3 is an plan view of a laboratory environment for measuring a human EEG.

First, as shown in FIG. 3, an experiment for measuring a human EEG was conducted in a laboratory under a mild environment which was shut off from the outside so that the human EEG could not be influenced thereby and in which the outdoor temperature/humidity and the indoor temperature/humidity were controlled. The laboratory mild environment includes an outer chamber 100 and an inner chamber disposed within the outer chamber 100. Here, an indoor unit 310 of a RAC is equipped to face the inside of the inner chamber 200, and an outdoor unit 320 of the RAC is installed to face one wall of the outer chamber 100 surrounding the inner chamber 200.

To measure a human EEG, a person 800 was positioned in front of the indoor unit 310 of the RAC at the center of the inner chamber 200. An EEG measuring apparatus 400 for measuring the EEG of the person 800 and a PC for EEG analysis 500 were disposed in the outer chamber 100. To measure the reaction of the person 800, an aural signal generator 600 for generating an aural signal was provided inside the inner chamber 200 at the right side of the person, and a time signal generator 700 for generating a time signal was provided in the inner chamber 200 in front of and facing the person 800.

EXAMPLE

In the working environment of the above described laboratory, standard temperatures (T1,T2,T3) were set to be 24° C., 26° C., and 28° C., respectively, and ranges of temperature variation with respect to the standard temperatures were set to be t1(1.0° C.), t2(1.5° C.), and t3(2.0° C.) to perform an EEG measurement.

Table 1 shows the general values of the human EEG used in this experiment.

TABLE 1

| E | F | A | A' | O |
|---|---|---|----|---|
| β | 14~25 HZ | 2~20 μV | alert, awake | nervous, tense, active |
| α | 8~14 HZ | 5~100 μV | awake, relax | engrossed, meditating |
| θ | 4~8 HZ | 5~100 μV | sleeping | between sleeping and conscious |
| δ | 0.5~4 HZ | 2~200 μV | sleeping | completely sleeping |

* E: EEG
F: frequency
A: amplitude
A': Awareness
O: occurring case

As shown in Table 1, each EEG wave has a respective frequency and amplitude, and the amplitude of β wave was measured in this example. As a result, when the EEG voltage is high, the alertness level is also high, which represents an optimum environment to effectively prevent drowsiness and to reinforce a studying efficiency.

The EEG wave enables judging the alertness level by its amplitude, and in analyzing the amplitude of the β wave in this experiment, the SPSS(Statistical Package for the Social Science) was adopted which is a package program for processing statistics.

Figure 5:
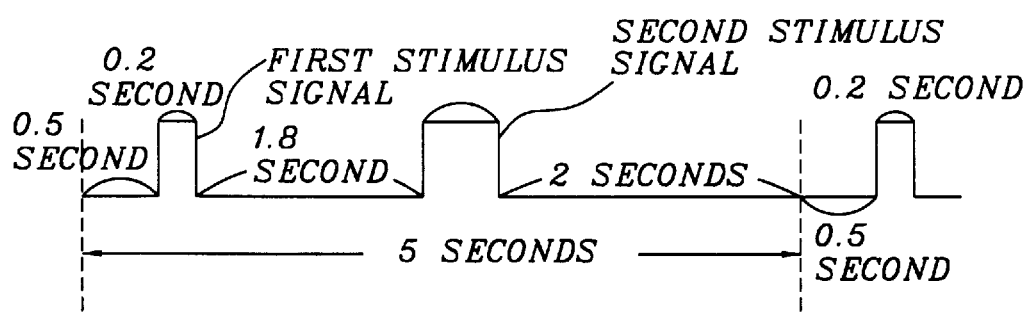
FIG. 5 is a pulse waveform diagram of an aural signal and a time signal used in measuring a human EEG.
Figures 4A, 4B:
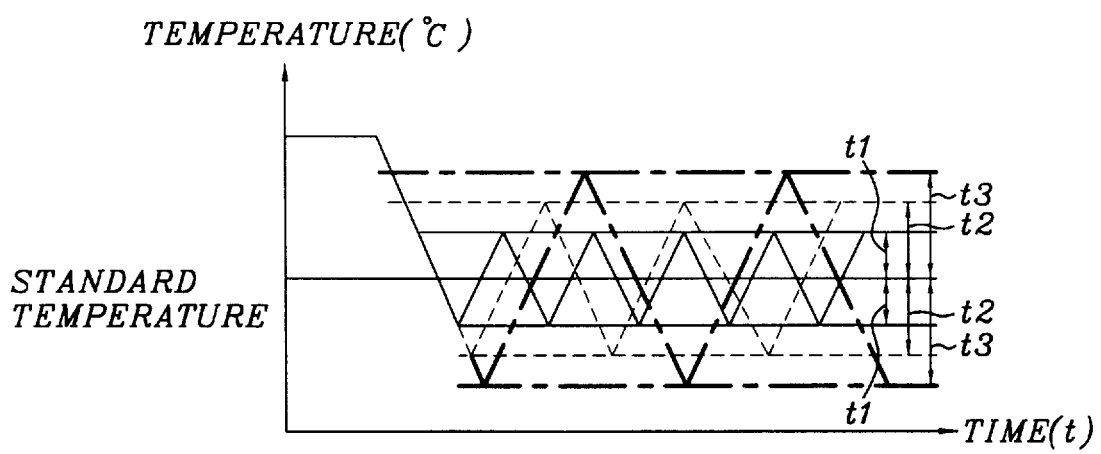
FIG. 4A is a table showing a standard temperature measured in the laboratory under a mild environment in FIG. 3 and a range of the temperature variation.
FIG. 4B is a graph showing a temperature characteristic of a thermocouple in the on/off operation of a compressor in a RAC according to the present invention.

Next, as shown in FIG. 5, the experimental method will be described using a protocol used in measuring an EEG. Here, the protocol is an agreement made between the experimenter and an experimental subject.

First, when a standard temperature is set to be 24° C.(T1), an EEG experiment is performed within the range of the temperature variation(t1,t2,t3) with respect to the first standard temperature (T1).

When a predetermined time passes after the RAC is operated, the aural signal generator 600 is controlled to generate an aural signal which serves as a first stimulus for 0.2 second. Next, after 1.8 second passes, a time signal generator 700 is controlled to generate a time signal which serves as a second stimulus for 0.5 second. Here, one section of a protocol that an aural signal and a time signal are generated is carried out for five seconds.

As shown in FIG. 5, when the aural signal sounds from the aural signal generator 600 in accordance with the protocol, the person 800 becomes tense for alertness. Then, after 1.8 seconds pass, time signals of "red light" and "green light" are turned on at random. The person pushes a button (not illustrated) corresponding to the lights placed in front of him/her in response to the time signals. Here, the person 800 must push the button with accuracy and promptness.

As described above, as the time and aural signals are generated for five seconds, the person 800 gives a response to the signals. At that time, an EEG of the person 800 is measured. The PC for EEG analysis 500 analyzes the EEG of the person 800 depending on the result of the measurement.

This experiment was conducted with the person's 800 eyes open, and the total number of the experimental subjects was six(three men, three women). The EEG of the person 800 in giving response to the aural and time signals was measured, and after 30 repetitions, the EEGs were collected and analyzed.

The EEG experiment was performed within the ranges of the temperature variation(t1,t2,t3) with respect to the standard temperatures T2 and T3 as well as T1.

Table 2 shows the result of the working experiment for achieving the optimum alertness under the conditions of the standard temperatures T1,T2,T3 and the ranges of the temperature variation t1,t2,t3.

TABLE 2

| T | | E C | R |
|---|---|-----|---|
| T1 | t1 | 24 ± 1.0° C., weak air | t1 > t3, t2 |
|    | t2 | 24 ± 1.5° C., weak air | |
|    | t3 | 24 ± 2.0° C., weak air | |
| T2 | t1 | 26 ± 1.0° C., weak air | t2 > t3 >> t1 |
|    | t2 | 26 ± 1.5° C., weak air | |
|    | t3 | 26 ± 2.0° C., weak air | |
| T3 | t1 | 28 ± 1.0° C., weak air | t1 >> t2, t3 |
|    | t2 | 28 ± 1.5° C., weak air | |
|    | t3 | 28 ± 2.0° C., weak wind | |

* T: temperature (°C.)
E C: experiment condition
R: result of statistics analysis Here, the amplitude of β wave was used as the analysis data. When the number of the analysis data was calculated, the formula was 154 points×30 trials×the number of experimental subjects, and the current condition of the RAC was a weak air operation. Here, one point represents the number of data, and when an EEG signal is inputted as a digital signal, 512 points per second can be inputted. However, 154 points were used in the analysis in the present example. In the result of statistical analysis, ">" means that the value is always larger with 90% reliability, and ">>" means that the value is always larger with 95% reliability.

As shown by the collected results in Table 2, when the standard temperature was T1, the range of temperature variation(t1) yielded the highest alertness level, and when the standard temperature was T2, the range of temperature variation (t2) yielded the highest alertness level, and when the standard temperature was T3, the range of temperature variation (t3) yielded the highest alertness level. In addition, when the standard temperature was T2 and the range of temperature variation was t2, the highest alertness level among all the other standard temperatures was recorded.

Referring to the above results, description will be given of the operating method for a RAC according to the present invention.

Figure 6:
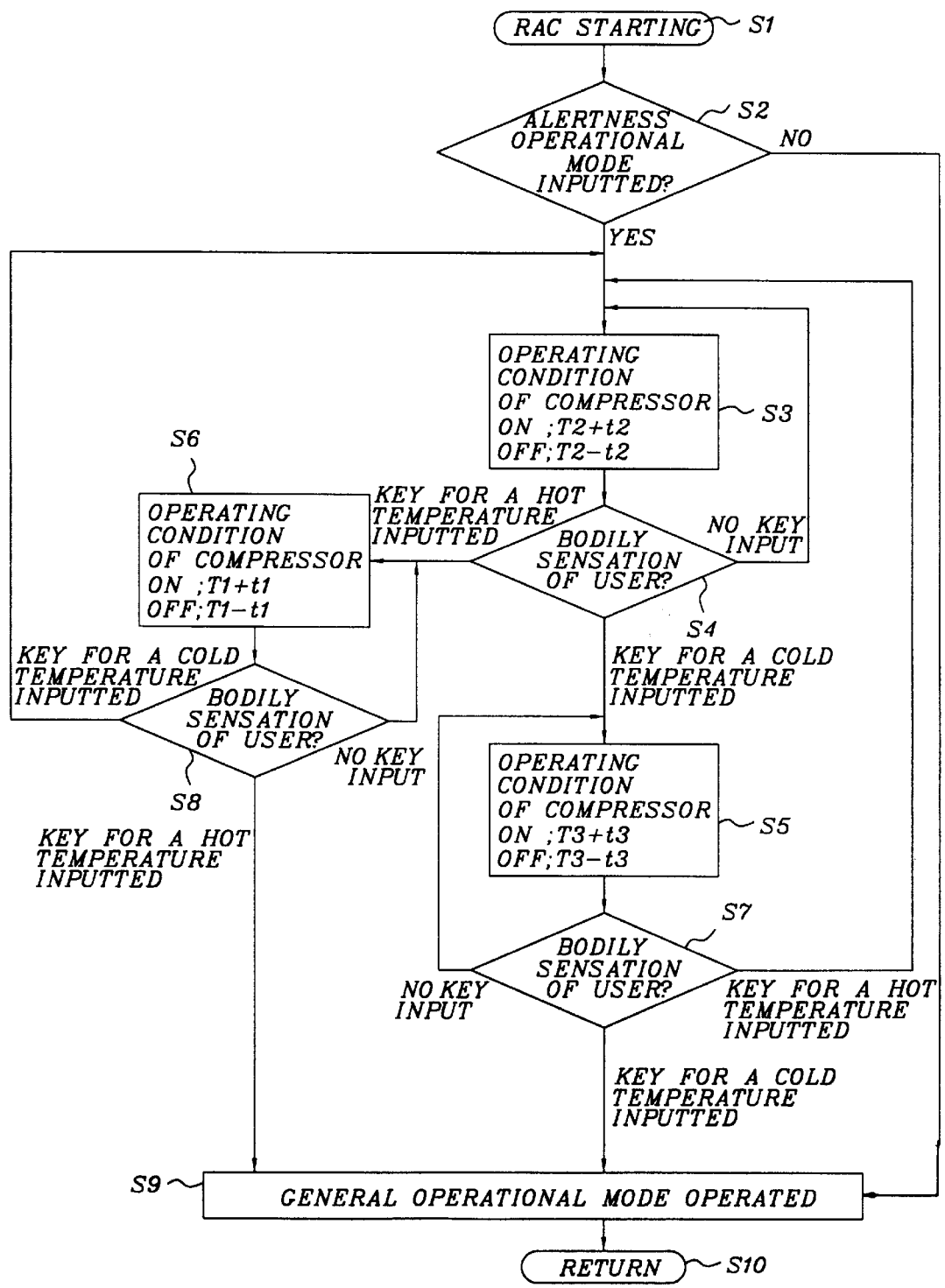
FIG. 6 is a flow chart of an operating method for a RAC according to the present invention.

As shown in FIG. 6, the RAC starts to be operated (S1), and the user inputs an alertness operational mode through a key input unit(not illustrated)(S2). The compressor is operated in accordance with the standard temperature T2 and the range of the temperature variation t2. At this time, if the alertness operational mode is not inputted, a general mode operation is performed (S9).

That is, the temperature at which the compressor is turned on is the standard temperature T2+the range of the temperature variation t2, and the temperature at which the compressor is turned off is the standard temperature T2—the range of the temperature variation t2.

Further, however high the alertness level of the user is, individual taste and temperature preference can have a different effect on a bodily sensation against the second standard temperature (T2). Therefore, the key input unit has keys for controlling the temperature suitably according to each temperature condition to achieve the optimum alertness mode.

In other words, when the user feels cold at the second standard temperature (T2), he can use the key for a cold temperature (S4). Then, the RAC starts the operation with the third standard temperature (T3) higher than the second standard temperature (T2) and the range of the temperature variation (t1)(S5). Here, the temperature at which the compressor is turned on is the third standard temperature (T3) +the range of the temperature variation(t1), and the temperature at which the compressor is turned off is the third standard temperature (T3)—the range of the temperature variation(t1).

Similarly, when the user feels hot at the second standard temperature (T2), he can use the key for a hot temperature (S4). Then, the RAC starts the operation with the first standard temperature (T1) lower than the second standard temperature (T2) and the range of the temperature variation (t1)(S6). Here, the temperature at which the compressor is turned on is the first standard temperature (T1)+the range of the temperature variation(t1), and the temperature at which the compressor is turned off is the first standard temperature (T1)—the range of the temperature variation(t1).

And, when the user feels cold at the first standard temperature(T1), he can use the key for a cold temperature. Then, the RAC starts the operation with the second standard temperature (T2) and the range of the temperature variation (t2)(S3). Conversely, when the user feels hot at the first standard temperature (T1), he can use the key for a hot temperature(S8) to operate the general mode(S9).

In addition, when the user feels hot at the third standard temperature(T3), he can use the key for a hot temperature (S7). Then, the RAC starts the operation with the second standard temperature (T2) and the range of the temperature variation (t2)(S3). Conversely, when the user feels cold at the third standard temperature (T3), he can use the key for a cold temperature(S7) to operate the general mode(S9), and thereby the operation of the air conditioner is repeated.

As described in detail above, according to the operating method for the RAC of the present invention, the RAC adopts a range of a temperature variation to provide the optimum alertness level according to each temperature region, thereby providing an optimum environment for enhancing an alertness level of a user, especially, a student to advantageously prevent drowsiness, and to improve studying efficiency.

Furthermore, since an alertness mode can be selected depending on individual taste and temperature preference, an agreeable working environment can be provided and the alertness level can be maximized.

Although the preferred embodiments of the present invention have been disclosed for illustrative purposes, those skilled in the art will appreciate that various modifications, additions and substitutions are possible, without departing from the scope and spirit of the invention as recited in the accompanying claims.

What is claimed is:

1. An operating method for a room air conditioner (RAC), the method comprising the steps of:

operating an air conditioning unit at a selected standard room temperature;

allowing a range of temperature deviations above and below the standard room temperature for enhancing an alertness level of the user; and controlling the deviations of the temperature above and below the standard room temperature based upon alertness levels measured in a human electroencephalogram (EEG).

2. The operating method of claim 1, wherein the EEG is determined at first, second and third standard room temperatures.

3. The operating method of claim 1, wherein the EEG is measured at a first standard room temperature and the range of the temperature variation, a second standard room temperature and the range of the temperature variation, and a third standard room temperature and the range of the temperature variation.

4. The method of claim 1, wherein the EEG measured is the amplitude of a $\beta$ wave.

5. The method of claim 1, wherein the EEG is measured according to an alertness testing protocol.

6. The method of claim 5, wherein the alertness testing protocol lasts 5 seconds.

7. An operating method for a RAC, comprising:

inputting an alertness-enhancing operational mode key command when it is desired by a user to heighten an alertness degree of the user;

performing an air conditioning operation for maintaining a first standard temperature and a range of temperature variation corresponding thereto to provide an optimum alertness degree in accordance with an alertness-enhancing operational mode;

performing an air conditioning operation to maintain a second standard temperature and the range of temperature variation corresponding thereto when the user feels cold at the first standard temperature, and to maintain a third standard temperature and the range of temperature variation corresponding thereto when the user feels hot at the first standard temperature;

repeating the second step when the user feels cold at the third standard temperature, and when the user feels hot at the second standard temperature; and performing an air conditioning operation in accordance with a general operational mode when the user feels hot at the third standard temperature, and when the user feels cold at the second standard temperature.

8. The method of claim 7, wherein the air conditioning operation is performed in accordance with the general operational mode if the alertness-enhancing operation mode key command is not inputted.

9. An electroencephalogram (EEG) measuring method for use in controlling a room air conditioner (RAC), the method comprising:

measuring an amplitude of a β-wave which is generated in an alert state in a human electroencephalogram (EEG) based on a first referenced temperature and a first temperature variation range with respect to the first referenced temperature, a second referenced temperature and a second temperature variation range with respect to the second referenced temperature, and a third referenced temperature and a third temperature variation range with respect to the third referenced temperature.

10. The method of claim 9, wherein said β-wave measuring is performed while an audio signal is generated after a predetermined time after an RAC is operated, and a time signal is generated after a predetermined time after the audio signal is generated.

11. The method of claim 9, wherein the measuring lasts for about five seconds.

* * * * *